US010359363B2

(12) United States Patent
Peumans et al.

(10) Patent No.: US 10,359,363 B2
(45) Date of Patent: Jul. 23, 2019

(54) TIME, SPACE DIGITALLY RESOLVED QUANTIFICATION OF LUMINESCENT TARGETS

(71) Applicant: IMEC VZW, Leuven (BE)

(72) Inventors: Peter Peumans, Herfelingen (BE); Liesbet Lagae, Leuven (BE); Willem Van Roy, Bierbeek (BE); Tim Stakenborg, Heverlee (BE); Pol Van Dorpe, Spalbeek (BE)

(73) Assignee: IMEC VZW, Leuven (BE)

( * ) Notice: Subject to any disclaimer, the term of this patent is extended or adjusted under 35 U.S.C. 154(b) by 22 days.

(21) Appl. No.: 15/736,414

(22) PCT Filed: Jun. 22, 2016

(86) PCT No.: PCT/EP2016/064441
§ 371 (c)(1),
(2) Date: Dec. 14, 2017

(87) PCT Pub. No.: WO2017/001262
PCT Pub. Date: Jan. 5, 2017

(65) Prior Publication Data
US 2018/0172587 A1 Jun. 21, 2018

(30) Foreign Application Priority Data

Jun. 30, 2015 (EP) .................................. 15174680

(51) Int. Cl.
*G01J 3/30* (2006.01)
*G01N 21/64* (2006.01)
(52) U.S. Cl.
CPC ..... *G01N 21/6408* (2013.01); *G01N 21/6456* (2013.01); *G01N 21/648* (2013.01)

(58) Field of Classification Search
CPC ............. G01N 21/6408; G01N 21/648; G01N 21/6456; G01N 33/54366; G01N 33/50;
(Continued)

(56) References Cited

U.S. PATENT DOCUMENTS

2008/0037008 A1 * 2/2008 Shepard ............. G01N 21/6408
356/73
2010/0197038 A1 8/2010 Verschuren

FOREIGN PATENT DOCUMENTS

WO 2008/092226 A1 8/2008

OTHER PUBLICATIONS

PCT Search Report and Written Opinion, PCT International Application No. PCT/EP2016/064441, dated Oct. 10, 2016, 14 pages.
(Continued)

*Primary Examiner* — Abdullahi Nur
(74) *Attorney, Agent, or Firm* — McDonnell Boehnen Hulbert & Berghoff LLP

(57) ABSTRACT

A sensor device for quantifying luminescent targets. The device comprises a light source for exciting the targets, thus generating luminescence signals, and a detector for detecting these signals of the targets in a cell, resulting in a detected signal comprising a desired signal and a background signal. The detector has a spatial cell resolution and/or a time resolution that is so high that only a limited number of targets will be present in the cell when measuring at low concentration and/or that only a limited number of targets add to the cell in between two measurements. A change in the number of targets in the cell can be observed in the detected signal. The device comprises a processor configured to distinguish the desired and the background signal, and to combine the detected signals of the different cells and/or moments in time, to quantify the targets.

11 Claims, 6 Drawing Sheets

(58) Field of Classification Search
CPC ........ G01N 30/74; G01N 21/75; G01N 33/58;
G01N 33/84; G01N 33/55; G01N 33/48;
G01N 33/57; G01N 33/68; G01N 33/53;
G01N 21/17; G01J 3/42
See application file for complete search history.

(56) References Cited

OTHER PUBLICATIONS

Chen, Yan et al., "The Photon Counting Histogram in Fluorescence Fluctuation Spectroscopy", Biophysical Journal, vol. 17. Jul. 1999, pp. 553-567.

* cited by examiner

TIME, SPACE DIGITALLY RESOLVED QUANTIFICATION OF LUMINESCENT TARGETS

CROSS-REFERENCE TO RELATED APPLICATION

The present application is a national stage entry of PCT/EP2016/064441 filed Jun. 22, 2016, which claims priority to European Patent Application No. 15174680.7 filed Jun. 30, 2015, the contents of which are hereby incorporated by reference.

FIELD OF THE DISCLOSURE

The present disclosure relates to the field of sensors, more particularly for instance biosensors. More specifically it relates to sensors making use of luminescence for quantifying a component in a solution.

BACKGROUND

Affinity based bio-sensors use an affinity probe which specifically binds to a target molecule. The target molecule is the molecule which comprises or consists of the analyte molecule that needs to be quantified. In affinity based bio-sensors the binding event is detected by a transduction scheme. This can be a direct detection of the binding event (e.g. in a label free sensor), or it may be an indirect chain of interactions that can be detected. In the last case a second probe with a label allows to obtain e.g. an optical or electrochemical signal representative for the amount of analyte being present. The label may for example be a fluorophore or an enzyme that catalyzes still another reaction that for example provides an optical or electrochemical signal.

In affinity based bio-sensors with fluorescence signal transduction, a bulk sample is sent over a surface, and the target molecule (analyte) is bound by an affinity probe on the surface. The presence of target molecules on the surface is thereby correlated with the presence of labels on the surface. These labels may for example be fluorescent. In such bio-sensors the fluorescent light is captured and its intensity is a measure for the amount of analyte molecules present in the original bulk sample. The affinity probe may for example be an antibody, an antigen, an aptamer, complementary DNA or a molecularly imprinted surface. In the affinity based fluorescent bio-sensor with evanescent excitation fluorescence, total internal reflection may be used to create an evanescent field very close to the sensor surface, to excite only those fluorophores which are present very close to the surface, and of a large fraction of which can be expected that they are bound to an affinity probe on the surface.

Despite the already existing affinity based sensors there is still room for building improved affinity based sensors.

SUMMARY

It is an object of embodiments of the present disclosure to provide optical detection systems with a good, e.g. an improved, signal to noise ratio. It is an objective of embodiments of the present disclosure to be able to separate the desired signal from background signal(s).

The above objective is accomplished by a method and device according to embodiments of the present disclosure.

The above objective is accomplished by a method and device according to the present disclosure.

In a first aspect, the present disclosure provides a sensor device for quantifying luminescent targets. The sensor device comprises:

a light source for exciting the luminescent targets, thus generating luminescence signals, a detector adapted for detecting the luminescence signals of the luminescent targets in a cell, resulting in a detected signal which comprises a desired signal originating from the luminescent targets in the cell and a background signal, wherein the detector has a spatial cell resolution and/or has a time resolution that is so high that only a limited number of luminescent targets will be present in the cell when measuring at low target concentration and/or that the time between two measurements is so small that only a limited number of luminescent targets add to the cell in between two measurements, wherein a change in the number of luminescent targets in the cell results in an observable change in the detected signal, a processor configured to distinguish the desired signal from the background signal, and to combine the detected signals of the different cells and/or different moments in time, so as to quantify the luminescent targets.

In example embodiments of the present disclosure, a change in the number of luminescent targets in the observed cell results in a change in the detected signal caused by a change of the desired signal which can be distinguished over the background signal. In example embodiments of the present disclosure, the cell size is so small that the total background level (and the fluctuations/uncertainty on this) drops, and the discrete events become distinguishable after processing by the processor. In example embodiments of the present disclosure, the background signal stays stable over a longer period of time than the time resolution of the detector. Luminescent targets add to the observed cell in between two sample moments will increase the desired signal with a discrete step. In example embodiments of the present disclosure, drift of the background signal which extends over the sampling moments can be cancelled out. In example embodiments of the present disclosure, by reducing the cell size the background signal decreases or that by reducing the time period between consecutive measurements the difference in background signal between the consecutive measurements decreases.

In embodiments of the present disclosure the spatial cell resolution is so high that only a small number of luminescent targets will be present in the cell when measuring at low target concentration and that the uncertainty on the desired signal when a luminescent target is present is smaller than the change in desired signal for a change in number of targets by one target.

In example embodiments of the present disclosure, when decreasing the cell size, below the size in which only one luminescent target can be present in the cell, the background signal decreases while the desired signal in the presence of one luminescent target remains the same.

In embodiments of the present disclosure the processor is configured to compare the measured signal of an observed cell with at least one adjustable threshold such that the exact number of luminescent targets present in the observed cell can be concluded.

In example embodiments of the present disclosure, a simple comparison is sufficient to decide on the presence of one or no luminescent target and/or to decide on the exact number of luminescent target(s) in a cell. By counting the number of cells in which a luminescent target is present, and by knowing the number of luminescent target(s) in a cell, the number of luminescent targets or the concentration of the luminescent targets in the original sample can be quantified. In example embodiments of the present disclosure, the presence of a luminescent target is digitized and/or that the absolute number of luminescent target(s) in a cell is digitized, and that also the measurement signal representative for the quantification of luminescent targets is digitized (counting the number of positive cells).

A sensor device according to embodiments of the present disclosure may comprise a surface or a three dimensional volume wherein the surface or the three dimensional volume comprises affinity probes for capturing the luminescent targets.

In example embodiments of the present disclosure, the eventual position of the luminescent targets is well defined. This allows to position the detector such that the monitored cells are on places where luminescent targets are expected. In example embodiments of the present disclosure, one binding event in a cell is sufficient to be detected by the detector for this cell.

A sensor device according to embodiments of the present disclosure may comprise an evanescent field generating structure, wherein the light source is coupled to the evanescent field generating structure and wherein the evanescent field generating structure is adapted for generating an evanescent field at the surface or in the three dimensional volume.

In example embodiments of the present disclosure, the illuminated volume is concentrated towards the luminescent targets and that therefore the background signal decreases whereas the desired signal remains the same when comparing with devices with free space illumination.

A sensor device according to embodiments of the present disclosure may be adapted for use with fluorescent targets.

In example embodiments of the present disclosure, the radiative lifetime of a fluorescent target is limited (e.g. around 5 ns or less). This allows to decrease the measurement time or to increase the number of measurements after which averaging can be applied.

In a second aspect, the present disclosure provides a method for quantifying luminescent targets. The method comprises:

exciting the luminescent targets, thus generating a luminescence signal, detecting per cell a measured luminescence signal, wherein the measured luminescence signal comprises a desired signal emanating from the luminescent targets in the cell and a background signal, wherein the detection is done on a cell space and/or time resolution which is so high that the total amount of luminescent targets/or the increase of luminescent targets with regard to the previous detection is limited, a discretizing step thereby obtaining a quantification, even an exact quantification, of the number of luminescent targets or the number of added luminescent targets per cell.

A method according to embodiments of the present disclosure may comprise statistical methods which are applied to the obtained target numbers over a plurality of cells and/or wherein the exciting, detecting, and discretizing steps are executed at a plurality of time points and wherein statistical methods are applied to the obtained target numbers at the plurality of time points so as to quantify the concentration of the luminescent targets in the original sample.

In example embodiments of the present disclosure, by applying statistical methods (e.g. Poisson statistics) the concentration of the luminescent targets in the original sample can be quantified.

A method according to embodiments of the present disclosure may comprise an averaging and/or smoothing step after the detection step wherein the averaging and/or smoothing step is applied on the data obtained by the at least ones executed excitation and detection step.

Particular aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

BRIEF DESCRIPTION OF THE FIGURES

FIG. 6 shows the measured signal which comprises the desired signal and the background in case of cell sizes of 100 area units in accordance with example embodiments.

FIG. 7 shows the measured signal which comprises the desired signal and the background in case of cell sizes of 10 area units in accordance with example embodiments.

FIG. 8 shows the measured signal which comprises the desired signal and the background in case of cell sizes of 1 area units in accordance with example embodiments.

FIG. 9 shows the measured signal which comprises the desired signal and the background in case of cell sizes of 0.3 area units in accordance with example embodiments.

Figure 1:
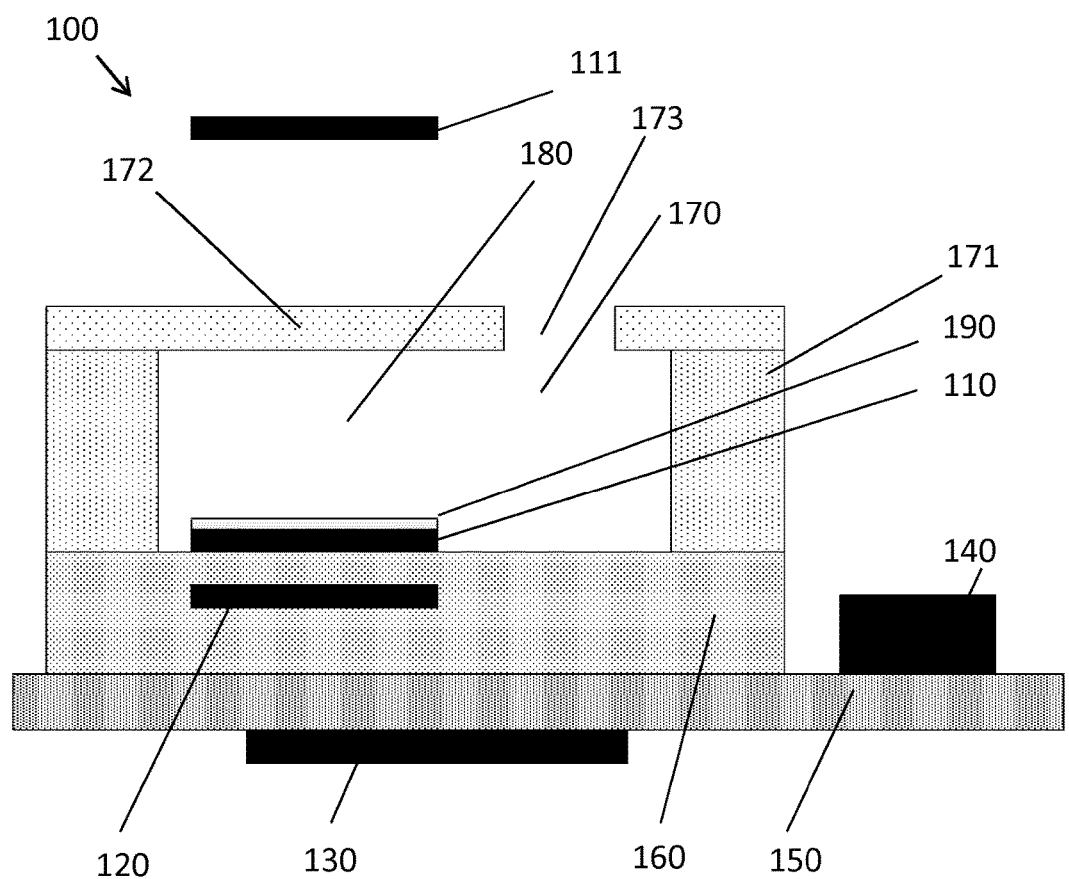
FIG. 1 is a schematic drawing of a device in accordance with embodiments of the present disclosure.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

As used herein and unless provided otherwise, the term "analyte" or "target" refers to the substance to be measured, the substance having or not having a biological origin. By the expression "substance having a biological origin", we intend to mean a substance that is present or produced in a living organism. Particularly, the substance may be a biomolecule. For instance, the analyte may be a protein or an antigen. The analyte may or may not be labeled for detection. In the context of the present disclosure, the terms target and analyte are considered to be synonyms.

By the term "biomolecule" is meant any molecule that is present in living organisms, including large macromolecules such as proteins, polysaccharides, lipids, and nucleic acids, as well as small molecules, such as primary metabolites, secondary metabolites, and natural products. The term "biomolecule" also encompasses molecules with similar properties and/or structure and/or composition, but that have been manufactured artificially rather than in a living organism.

Where in embodiments of the present disclosure reference is made to "luminescence of a target", reference is made to emission of light by the target, not resulting from thermal emission. Typically, in the context of the present disclosure, luminescence will be photoluminescence, generated by absorption of photons; such as fluorescence or phosphorescence. The present disclosure, however, is not limited to this type of luminescence, and can also be applied in case of, for instance, bioluminescence or chemiluminescence (emission as a result of a (bio)chemical reaction by an organism) or electroluminescence (a result of an electric current passed through the target).

Where in embodiments of the present disclosure reference is made to the "background signal", reference is made to any signal which is disturbing the measurement of the desired signal. This may comprise background signals from luminescent sources which do not form part of the target under study. This may comprise luminescence which is scattered by scattering centers in the device. This may comprise any other noise source which is present in the device.

Where in embodiments of the present disclosure reference is made to "quantifying luminescent targets", reference is made to either determining the presence of luminescent targets, or determining the amount of luminescent targets, or determining the concentration of luminescent targets.

Where in embodiments of the present disclosure reference is made to "a cell" reference is made to a subdivision of the monitored volume or area of the sensor device.

Where in embodiments of the present disclosure reference is made to "an event", reference is made to a luminescent target which enters a cell observed by the detector. In embodiments of the present disclosure this may be caused by a luminescent target that binds with a surface of the sensor device.

Where in embodiments of the present disclosure reference is made to "an area unit" reference is made to the size of an observed cell. In embodiments of the present disclosure the size of the observed cell is so small that individual (discrete) binding events are expected to occur after a given incubation time. This may be at equilibrium or at a fixed time before equilibrium. This may mean that at low target concentration, e.g. at or around the limit of detection, and/or for a specific accumulation time only a small fraction of the capture sites will be occupied.

Where in embodiments of the present disclosure reference is made to "a limited number of luminescent targets", reference is made to a number of targets that is small enough such that they can be assigned absolutely/digitally. The limited number may be smaller than or equal to 20, or even smaller than or equal to 10, or even smaller than or equal to 3, or even smaller than or equal to 1

In a first aspect, the present disclosure provides a device 100 for quantifying targets (analyte) which may be present in a fluid sample, e.g. in a biological fluid such as a blood sample, a urine sample, a drop of saliva, sperm. One embodiment of such device 100 is schematically illustrated in FIG. 1. Devices according to embodiments of the present disclosure may comprise a microfluidic channel 170 for guiding the sample towards a cavity 180 in or on a substrate 160, for instance a semiconductor substrate such as e.g. a silicon substrate or a transparent substrate such as e.g. a glass substrate. The microfluidic channel 170 and/or the cavity 180 may have sidewalls 171 and top 172, inlet(s) and/or outlet(s) 173. These sidewalls 171, 172 and/or inlets/outlets 173 may be transparent or opaque. The cavity 180 and the microfluidic channel 170 may be the same. The cavity 180 may comprise a surface 190 on which affinity probes may be present for capturing the target molecule. In embodiments of the present disclosure the analyte may be luminescent (e.g. fluorescent) itself or it may be labeled with a luminescent label.

In embodiments of the present disclosure the sample may be injected in the device as a one-time event (e.g. filling a reservoir) or the injection may be a continuous event (e.g. triggered by starting a flow) that continues during the subsequent steps when quantifying the targets.

In embodiments of the present disclosure the luminescent targets may be illuminated through (regular) free space illumination or through evanescent illumination. In free space illumination light source 111 is illuminating at least the surface 190 with the affinity probes. The light source 111 may be located at the top (the top wall 172 and any other layer between the light source 111 and the cavity 180 should be transparent) or bottom (the substrate 160 and any other layer between the light source 111 and the cavity 180 should be transparent) of the device 100. The light source 111 may be, amongst others, a laser, a laser diode, a VCSEL, a LED, a lamp, a Tungsten lamp, a Halogen lamp, a Mercury lamp, a Xenon lamp, a Metal Halide lamp. In embodiments of the present disclosure the light coming from the light source 111 may be projected or focused by lenses or mirrors or a microscope or optical fibers on the surface 190. (In this case no evanescent field generating structure 110 is present).

In case of evanescent illumination, devices according to embodiments of the present disclosure comprise an evanescent field generating structure 110 for generating an evanescent field at the surface 190.

The evanescent field generating structure 110 may be integrated in or on the substrate 160 or it may be separate from the substrate 160 (e.g. against the microfluidic channel top 172 or sidewalls 171). In embodiments of the present disclosure the light of the light source 111 may be guided towards the cavity 180 using a connecting structure such as an optical waveguide 130. The light may be coupled to the evanescent field generating structure 110 or to the connecting structure using any suitable optical device, such as for instance a grating coupler or a butt coupler.

In embodiments of the present disclosure the light source 111 may be integrated in the substrate 160. In case of close integration with the rest of the device 100, the light source 111 may be, amongst others, a laser, a laser diode, a VCSEL, a LED. These light sources may be applied in the case of evanescent excitation.

In case the light source 111 is not necessarily closely integrated with the rest of the device 100 it may also be a laser, a lamp, a Tungsten lamp, a Halogen lamp, a Mercury lamp, a Xenon lamp, a Metal Halide lamp. This type of light source can also be applied in the case of evanescent excitation.

Devices 100 according to embodiments of the present disclosure moreover comprise a detector 120 which can detect the luminescence of the luminescent target after the target has been excited with the evanescent field generating structure 110 or light source 111. The measured signal is composed of a desired signal which originates from the luminescent targets and a background signal emanating from other luminescent sources present in the system. The detector 120 may be located external to the cavity 180 (not integrated in/in physical contact with either substrate 160 or top 172). In that case at least one top or bottom wall (e.g. walls from the microfluidic channel 171, 172, substrate 160, any other layer) should be transparent such that the luminescence signals from the luminescent targets can exit from the cavity through this wall. In case the detector is located external to the cavity additional lenses, as used in classical optics, may be applied for guiding the luminescence signals towards the detector.

In embodiments of the present disclosure the detector 120 may be integrated with the cavity 180. It may be present at the top or at the bottom of the cavity. The bottom side is the side where the target molecules bind to the affinity probes, the top side is the opposite side thereof. The detector 120 may be present on the inside or the outside of the cavity. When on the outside a transparent wall of the cavity is required.

In embodiments of the present disclosure luminescence from the luminescent targets may be collected by a waveguide connected to the detector 120. This waveguide may be the same as the excitation waveguide, or it may be a different waveguide. The luminescent light may be coupled from the waveguide into the detector 120 the same way as the light coming from the light source is coupled into the waveguide (e.g. through a grating coupler, butt coupling etc.). This may be the same coupler as the input coupler, if it has enough bandwidth and if incoming and outgoing light is handled appropriately, or it may be a different coupler. In embodiments of the present disclosure the input coupler and the output coupler are different. In embodiments of the present disclosure diffraction and/or reflection optics may be present between the waveguide and the detector. This may for example be a lens to project the output couplers onto the detector. Filters may be present, in, on or before the detector, for attenuating light which is outside the frequency range of the light generated by the luminescent targets. The detector 120 may be a CMOS imager.

In embodiments of the present disclosure the area or volume observed by the detector is subdivided in a number of observed cells 310. In embodiments of the present disclosure the measured signal is composed of a desired signal which originates from the luminescent targets which are present in an observed cell 310 and a background signal emanating from other luminescent sources present in the system. In embodiments of the present disclosure the cell size is so small that only a limited number of luminescent targets are expected to be present in the observed cell. In embodiments of the present disclosure the cell size is thereby decreased so much that the desired signal (after processing) becomes larger than the background signal.

Embodiments of the present disclosure comprise a surface 190 provided with affinity probes for binding the luminescent targets.

In embodiments of the present disclosure, mainly the surface 190 of the substrate 160 or a three dimensional volume is illuminated. In these embodiments the bulk of the sample is not illuminated using free space light but using an evanescent light near the surface 190. The evanescent field region may have a thickness of a few nm-thick or even 10 nm thick or even between 10 nm and 100 nm thick. This may be done by evanescent excitation. Such evanescent illumination is also referred to as TIRF (total internal reflection fluorescence). This can be achieved by having a beam of light, coming from the evanescent field generating structure 110, incident on the interface between the evanescent field generating structure 110 and the cavity 180 at an incident angle below the critical angle, resulting in a total internal reflection. It can also be achieved by confining the light in a guiding structure such as a waveguide. TIRF can be applied in example embodiments of the present disclosure. Only the luminescent labels (e.g. fluorophores) which are immobilized at the surface 190 of the substrate evanescent field generating structure 110, or which are in its immediate neighbourhood (i.e., within the range of the evanescent field) will be illuminated this way. The substrate 160, on which evanescent field generating structure 110 is fabricated may be a semiconductor substrate, a glass substrate, or any other suitable type of substrate. It may be a quartz substrate. Luminescent labels which are in the bulk solution are thereby not measured. When these luminescent labels in the bulk solution are not excited they will also not generate a background signal.

Embodiments of the present disclosure comprise a waveguide for guiding the excitation light towards the evanescent excitation plane. In example embodiments of the present disclosure, the luminescent labels (e.g. fluorophores) in the bulk solution will not be excited. Only the luminescent labels which are in the evanescent field volume will be illuminated. These luminescent labels are mainly the surface immobilized luminescent labels. The labels in the bulk, which are not illuminated or which are less illuminated than the immobilized labels at the surface, will therefore generate a smaller luminescent signal than the immobilized labels at the surface. It is an example of embodiments of the present disclosure, by only illuminating the evanescent excitation plane, the signal to noise ratio can be increased.

In embodiments of the present disclosure the surface 190 may be divided into a plurality of cells, and/or the time between consecutive measurements may be made so small such that the number of binding events in a cell is discrete, for example smaller than 20, smaller than 10, smaller than 3, or even digital (0 or 1). Such a cell may have size below 10 µm², below 1 µm² or even down to 0.3 µm². In example embodiments of the present disclosure, the number of bound luminescent targets can be absolutely (and hence very accurately) determined.

Each of the cells 310 is observed by a detector 120. In embodiments of the present disclosure, the detector 120 may be a single detector. In embodiments of the present disclosure the detector may also be a (group of) pixel(s) of a line detector or a (group of) pixel(s) of an imager comprising multiple pixels. The detector may be a CMOS detector, a CCD detector, a(n array of) photodiode(s), an (array of) avalanche photodiode(s), a(n array of) photomultiplier tube(s) PMT(s).

In embodiments of the present disclosure the time between two consecutive measurements, performed by the detector, of an observed cell is significantly smaller than the average time between the capture of two consecutive (labelled) targets. This can be achieved by reducing the time between successive measurements and/or decreasing the size of each cell (which increases the average time between the capture of two consecutive (labelled) targets in the cell). In embodiments of the present disclosure the time between two consecutive measurements is decreased so much that a change in the desired signal caused by adding a labelled target to the cell becomes larger than the uncertainty on the signal level in between the binding events. In embodiments of the present disclosure the uncertainty on the signal level in between the binding events is reduced by averaging or smoothing or other data analysis techniques including wavelet-based techniques.

Embodiments of the present disclosure comprise a processor 140 which is configured to process the detected signals, thereby increasing the signal to noise ratio so much that the desired signal originating from individual luminescent targets can be distinguished.

The term processor 140 should be interpreted widely. It can be a microprocessor but it can for example also be an ASIC (application specific integrated circuit) or an FPGA (field programmable gate array), or an analog or digital signal processing device. The processing may be distributed. It may for example be partly or completely running on an external device (e.g. a smartphone). The external device, e.g. smartphone, may for example receive raw data (digitized output of the detector) or it may receive already pretreated data.

In embodiments of the present disclosure the detected signal is averaged or smoothed to distinguish the desired signal from the background signal. In example embodiments of the present disclosure, the desired signal can be distinguished from the averaged detected signal by looking at the discrete offsets in the averaged or smoothed detected signal. When averaging or smoothing the detected signal, the uncertainty on the averaged or smoothed background signal will decrease. It is sufficient to continue averaging until the discrete steps of the desired signal become visible. The baseline (the desired signal) per cell is therefore reduced to a discrete number of signal levels. Averaging or smoothing the detected signal will result in an averaged or smoothed signal which changes in discretely discernible steps corresponding to the number of binding events in the concerned cell.

A device 100 according to embodiments of the present disclosure may be present on a printed circuit board 150. It may comprise a needle or a suction element like a cotton strip (not illustrated) and a microfluidic channel 170 for taking or receiving a fluid sample and guiding it to the surface 190. In example embodiments of the present disclosure, the different features required for executing the steps for analyzing a fluid sample may be integrated in one and the same device 100.

Depending on the embodiment, the fluidics of the device 100 can be different. They can for example be capillary and/or they can be pressure driven, e.g. pumped. Pumps can for example control the pressure or the volumetric flow rate. The microfluidic channel 170 can be an open channel or a closed channel. A schematic drawing of a device 100 in accordance with embodiments of the present disclosure and comprising the features as described above is shown in FIG. 1.

The size of the device 100, in accordance with embodiments of the present disclosure, is limited. The size may for example be comparable to the size of an SD-card or of a micro-SD card or of a USB-stick.

Embodiments of the present disclosure can for example be used to check if certain biomarkers are present in the fluid (e.g. presence of antibodies against HIV in a blood sample).

In embodiments of the present disclosure the background signal may have different origins. Luminescent sources may be present which are not linked with the analyte, hence which do not form part of target molecules. These will, nevertheless, be detected by the detector 120 and will increase the background signal of the device 100.

Figure 2:
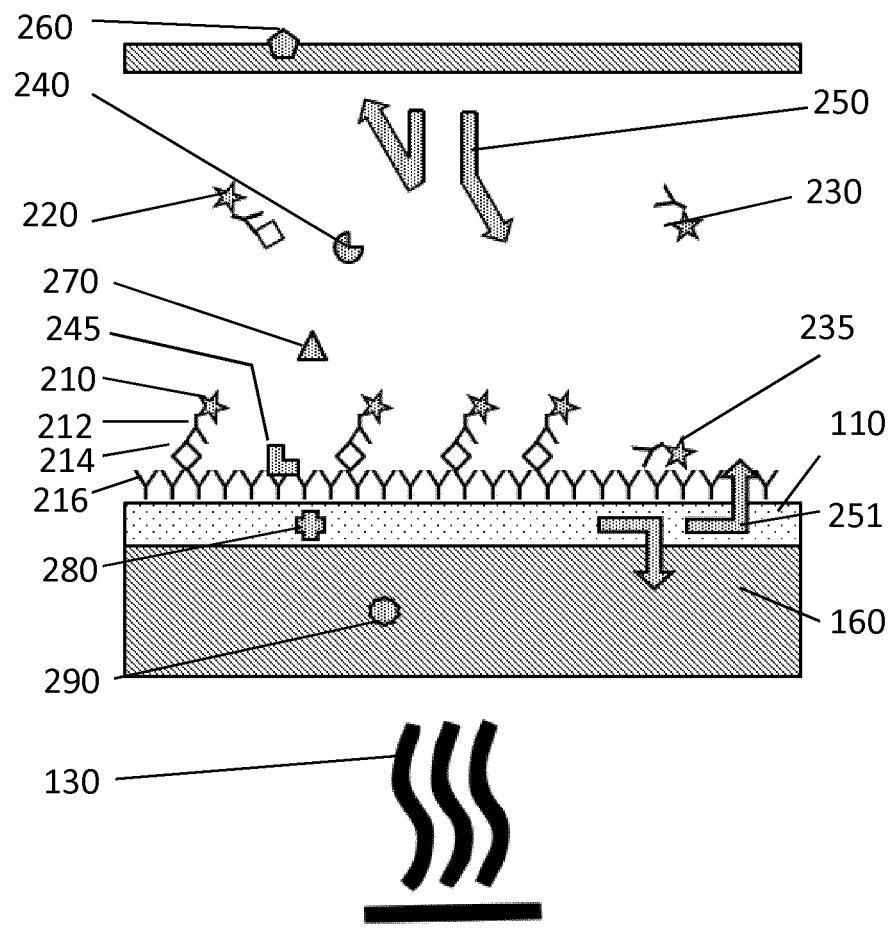
FIG. 2 is a schematic drawing illustrating the origin of desired and background signals in a device in accordance with embodiments of the present disclosure.

In an exemplary embodiment of the present disclosure, illustrated in FIG. 2, the device detector 100 is based on a sandwich ELISA like assay. The disclosure, however, is not limited thereto, but may for instance also be based on competitive assays and inhibition assays, where analogous sources of background are present. In a sandwich assay the target may comprise luminescent labels that are fluorescent labels or may be attached to luminescent labels that are fluorescent labels. A fluorescence signal which is coming from a target which is bound to the surface 190, whereby the target comprises fluorescent analyte, or a fluorescent label which is bound to the analyte, is part of the desired signal. In fluorescence detection, fluorescent signals coming from labels in the bulk are to be avoided. In example embodiments of the present disclosure which comprise an evanescent field generating structure 110, contribution of these signals can be reduced. Sources of the desired signal and of background signals in a device 100 comprising a sandwich ELISA like assay, according to embodiments of the present disclosure are illustrated in FIG. 2. FIG. 2 shows a sketch for the case of pre-incubation. In that case in a first step the detection probe (e.g., detection label) are mixed with the analyte. In a next step this mixture flows over the surface 190 with the capture probes. Real-time measurements can be performed, in which the rate at which the target binds to the surface can be followed. In this example the origins of the desired signal are the labels 210 indicated by a star which are connected to the targets 214 indicated by a rhombus and which are bound to the surface 190. In the example the labels 210 are fluorescent labels which are linked to a second affinity probe (e.g. second antibody 212). The second antibody 212 is linked to a target 214 which is linked with a first affinity probe (e.g. first antibody 216). The first antibodies 216 are forming the surface 190 on top of the evanescent field generating structure 110. Instead of a surface 190, in other embodiments of the present disclosure, the targets may be bound in a 3D-matrix or gel. In that case the first affinity probes are immobilized in a 3D matrix or gel. In the pre-incubation the labels 220 are those labels which are already connected with a target 214 but are not yet caught on the surface 190. In this figure the targets 214 have a rhombus shape, the detection probes (e.g. second antibodies) 212 have an inverse Y-shape and the capture probes (e.g. capture antibodies) 216 have a Y-shape. In such a device 100, besides other noise sources, the background signal may be coming from:

(Auto)Fluorescent molecules 245, including labels 235 which are (non-specifically) bound to the surface 190 and which are not connected with the targets 214. These are illustrated by the L-shaped symbol in FIG. 2. These also include the labels 235 which are bound to the second antibody 212 and to the surface 190, but wherein the second antibody 212 is not bound to the target 214.

(Auto)Fluorescent molecules 240 in solution. The (auto) fluorescent molecules 240 which have no link with a second antibody are illustrated by the pie-shape symbol in FIG. 2. They may for example be proteins. They mostly come from the sample, but can also come from the detection antibody mix, or the blocking agents (e.g. BSA). (Auto)Fluorescent molecules 240 are molecules that cannot be avoided, as they are part of the sample or a key ingredient in the assay. They may or they may not be:

Free labels 230 in the solution which are bound to the second antibody 212 but wherein the second antibody 212 is not bound to the target 214. These labels 230 are intentionally fluorescent, and they are present in a real-time (wash-free) assay. These labels 230 are not present in an endpoint assay, after washing.

Labels 220 in the solution which are bound to the second antibody 212 and wherein the second antibody 212 is bound to the target 214. These labels 220 are intentionally fluorescent, and they are present in a real-time (wash-free) assay. These labels 230 are not present in an endpoint assay, after washing.

(Auto)Fluorescent centers 270 in the solution. The triangle in FIG. 2 is an illustration of such a fluorescent center. These centers are present in the buffer (the solvent) itself (i.e. the matrix wherein the (bio)molecules are present). These centers may for example be present in a buffer used in a bioreactor (when using a device 100 according to embodiments of the present disclosure in the bioreactor). In that case the buffer may be the cell culture medium which can have a complex composition and may comprise components that show luminescence (e.g fluorescence). Often additional components are added depending on the exact nature of the cells/bacteria/yeasts/tissue that is cultured. These centers 270 will stay also when changing to buffer flow whereas the autofluorescent molecules 240 are absent in the buffer.

(Auto)Fluorescent centers 280 in the structure for generating an evanescent field 110. The cross in FIG. 2 is an illustration of such a fluorescent center.

(Auto)Fluorescent centers 290 in the substrate 160. The circle in FIG. 2 is an illustration of such a fluorescent center.

(Auto)Fluorescent centers 260 in any other part of the device 100. The pentagon in FIG. 2 is an illustration of such a fluorescent center.

Scattering 250, 251 of the excitation light. The arrows 250, 251 in FIG. 2 illustrate the scattering of the excitation light in case of free space excitation (250, e.g. illumination through a lens) and in the case of excitation using an evanescent field (251, e.g. using a waveguide). The scattering may e.g. be caused by imperfections or discontinuities in the device or the sample. Embodiments of the present disclosure comprise for example a rejection filter for filtering out the direct and/or reflected and/or scattered excitation light. However, the rejection ratio of this filter is not infinite and therefore a part of the scattered excitation light reaches the detector.

These background signals increase the noise and therefore decrease the signal to noise ratio, while it is desired to have the signal to noise ratio as large as possible.

Instead of pre-incubation, another approach would be to first send over the analyte, wash to remove any unbound particles, then send over the labelled detection probe, and wash again. In that case, some background sources are different/absent (e.g. the labels 220 would not be present, and some (auto)fluorescent molecules 240 would not be present in the detection probe). However, in this approach we cannot do real-time measurements, so the time-to-response is longer)

Embodiments of the present disclosure are not limited to the standardized enzyme-linked immunosorbent assay (ELISA) as illustrated in FIG. 2 or its variants, but include any affinity-based assay and can for example also be DNA based. The DNA measurements may comprise a PCR step and may involve a higher fluorophore concentration.

Figure 3:
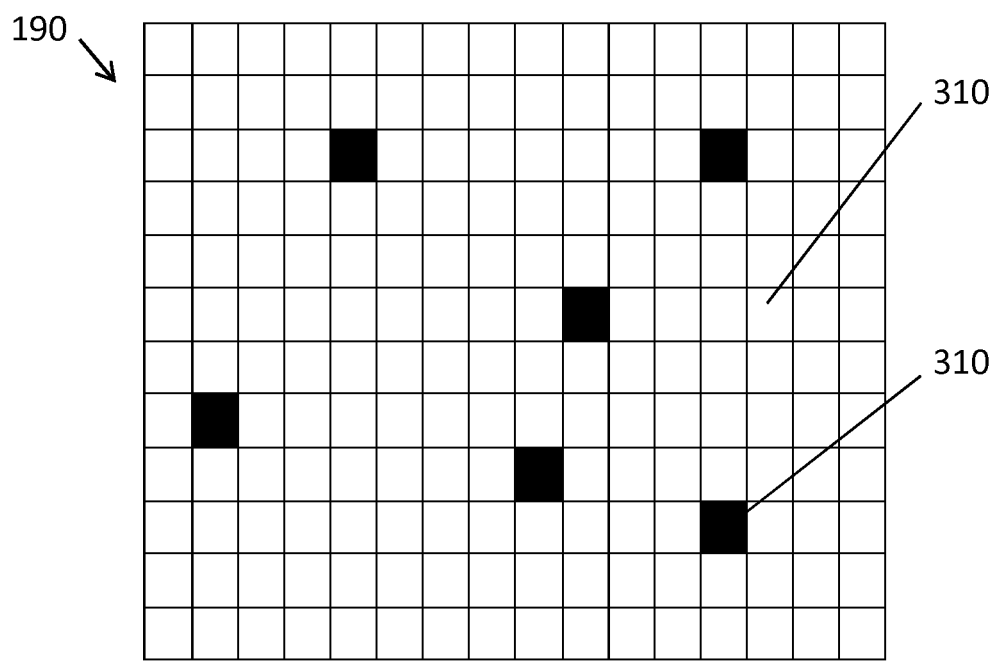
FIG. 3 is a schematic drawing of a surface subdivided in observed cells in accordance with embodiments of the present disclosure.
Figure 4:
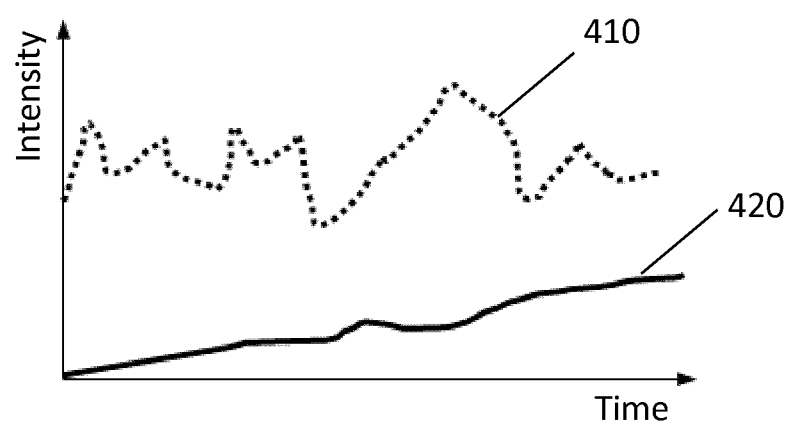
FIG. 4 shows a desired signal and a background signal in function of time in accordance with example embodiments.

FIG. 3 shows a surface 190 subdivided in cells 310 in accordance with embodiments of the present disclosure. When observing the surface 190 as a whole, this may result, over time, in a background signal 410 and a desired signal 420 as plotted in FIG. 4, wherein the intensity in function of time is shown. For each new binding event the desired signal is increasing by an amount that is smaller than the uncertainty on the background signal, even after application of data analysis techniques such as averaging, smoothing, or other, to reduce the uncertainty.

Figure 5:
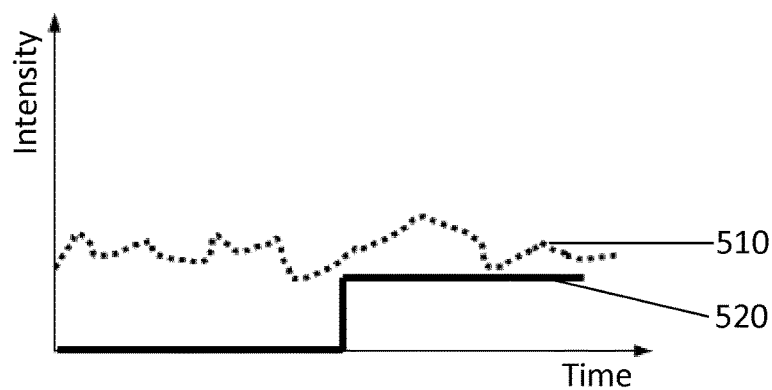
FIG. 5 shows a desired signal and a background signal in function of time for an observed cell with reduced cell size in accordance with embodiments of the present disclosure.

The cells in FIG. 3 may for instance have a size such that only zero or one luminescent target is expected to bind to any cell 310 during the timeframe of interest. When observing the cells 310 individually, the desired signal can only have two values: either the luminescent target is present or it is not. This is illustrated in FIG. 5, showing the background signal 510 and the desired signal 520. In the beginning of the measurement no luminescent target is present resulting in a desired signal 520 with zero intensity. After a luminescent target gets bound to the observed cell 310 the desired signal 520 increases with a discrete step which is larger than the uncertainty on the background signal, especially after data analysis techniques such as averaging, smoothing, or other, have been applied to reduce the uncertainty.

In embodiments of the present disclosure the number of bound molecules is statistically distributed (a typical distribution is the Poisson distribution). Statistical analysis may then be applied to the detected signals coming from the large number of sub-areas (cells) to determine the unknown target concentration that was applied to the sensor device.

FIG. 6 to FIG. 9 simulate the effect of decreasing the cell size on the measured signal and the standard deviation thereon. The following parameters were assumed:
  on average one luminescent (e.g. fluorescent) target is bound per unit area (e.g. per 1 $\mu m^2$);
  on average ten background generating molecules (e.g. fluorophores) are present per unit area;
  both the desired signal as well as the background signal are assumed to follow a Poisson distribution.

For each of the different figures ten independent time traces were simulated. For each time trace the number of bound luminescent targets was chosen randomly (Poisson), but remained constant within the trace. These measurements can for example represent:
  successive time periods of a time-dependent measurement, wherein the length of a period is shorter than the time between successive binding events;
  snapshots at the end of incubation such that the number of bound luminescent targets does not increase.

On average ten background molecules were present per unit area. The exact number was chosen randomly at every time step according to a Poisson distribution. This simulation can for example represent bulk fluorophores moving in and out of the sensing volume or non-specifically bound molecules binding to and unbinding from the sensor surface 190 where the integration time is shorter than the characteristic time scale at which the background events fluctuate. At longer integration times the background events are (partially) averaged out, such that the random changes would be smaller than in the present simulations.

The left graphs of FIGS. 6 to 9 show ten time traces of 128 points each on an arbitrary time scale. The right graphs show the average value of the 128 time points in each time trace, the standard deviation on the individual time points (large error bars, thin lines 610), and the uncertainty on the average value (small error bars, thick lines 620). As the number of bound targets does not vary within a time trace, these standard deviations and uncertainties are entirely due to the random nature of the background events.

Figure 6:
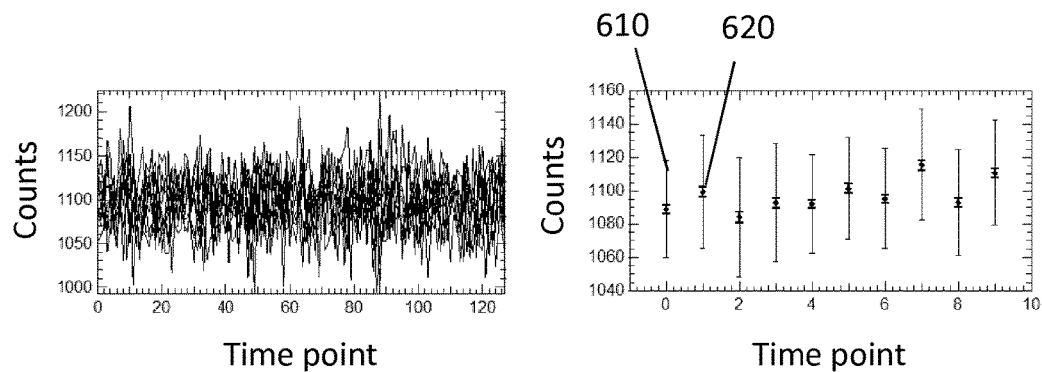
FIG. 6-FIG. 9 simulate the effect of decreasing cell size on the measured signal which comprises the desired signal and the background signal, the standard deviation thereon, and the uncertainty on the averaged signal in accordance with embodiments of the present disclosure. The average signal is 1 count per area unit, the average background is 10 counts per area unit, and both follow a Poisson distribution. The left figures show 10 time traces of 128 points. The right figures show the average and standard deviation thereof.

In FIG. 6 the cell size is 100 area units (e.g. 100 $\mu m^2$). This corresponds with an average desired signal of 100 counts and an average background signal of 1000 counts.

Figure 7:
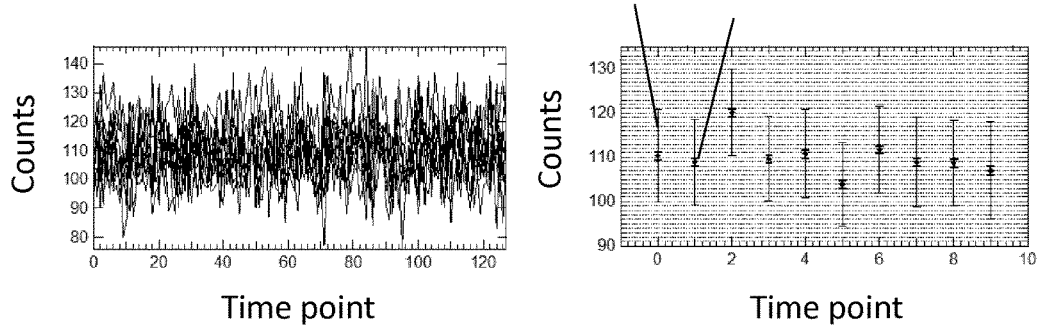

In FIG. 7 the cell size is 10 area units (e.g. 10 $\mu m^2$). This corresponds with an average desired signal of 10 counts and an average background signal of 100 counts.

Figure 8:
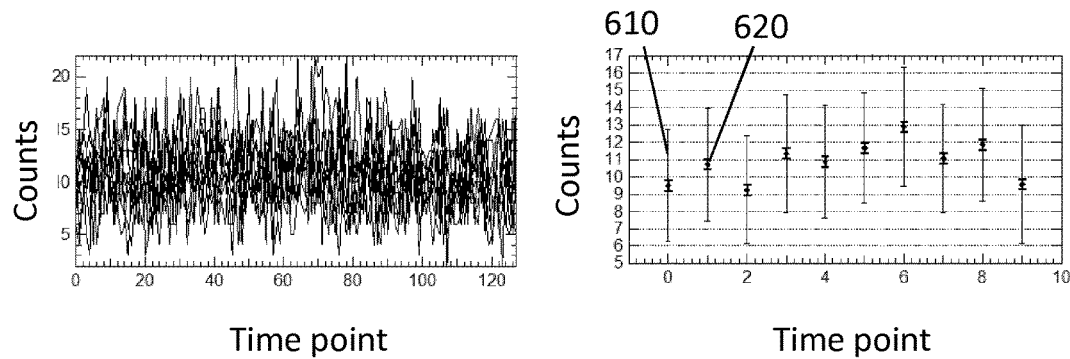

In FIG. 8 the cell size is 1 area units (e.g. 1 $\mu m^2$). This corresponds with an average desired signal of 1 count and an average background signal of 10 counts.

Figure 9:
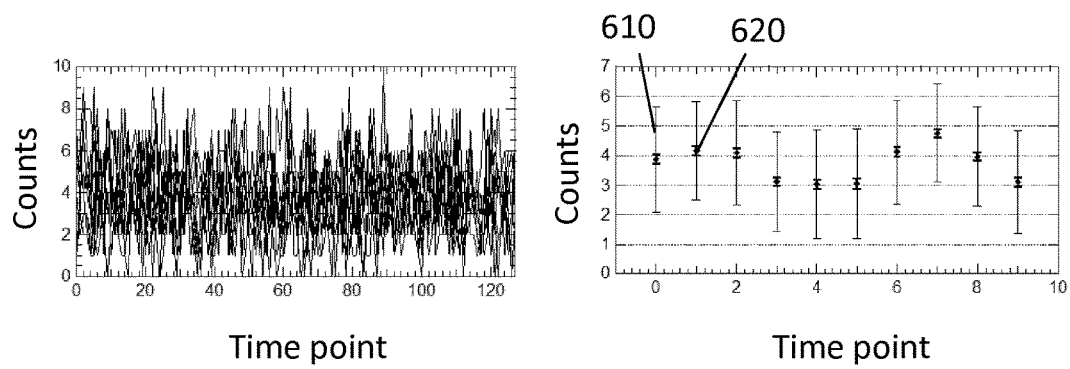

In FIG. 9 the cell size is 0.3 area units (e.g. 0.3 $\mu m^2$). This corresponds with an average desired signal of 0.3 counts and an average background signal of 3 counts.

For the large cell sizes (with large desired signal counts, e.g. with a desired signal count of 100 or 10), the uncertainty on the average values is much larger than 1. As a consequence, the average value cannot be accurately determined.

For the small cell sizes (with small desired signal counts, e.g. in this exemplary embodiment of the present disclosure with a desired signal count below 1, for instance about 0.3), the uncertainty on the average values becomes comparable to or smaller than 1. Since the total number of bound molecules is an integer, the average can be assigned to a discrete level without any remaining uncertainty.

For example in FIG. 9 the following counts can be obtained: 4-4-4-3-3-3-4-5-4-3. As a result, the averages can be assigned exactly to those discrete levels and the noise associated with the varying background can be completely eliminated.

It will be noticed that these counts correspond to a (variable) number of bound molecules, and a number of background events that is unknown but that is equal for all time traces within an uncertainty of less than 1 count. However, the relative number of cells with 0, 1, 2, 3, . . . bound molecules follow a Poisson distribution. If a sufficiently large number of cells is measured, this distribution can be used to determine the level of the desired signal and the level of the background signal that corresponds to zero bound molecules (in many cases, this will be simply the lowest of the discrete levels), and hence also the averaged background count number and the exact number of bound target molecules in each cell.

In example embodiments of the present disclosure, this leaves only the statistical variation of the number of bound molecules on every small cell, which is the result of the random nature of the capturing of the targets. It is known that the behavior of this random process is well described by Poisson statistics. In example embodiments of the present disclosure, by measuring a sufficient number of small cells the unknown target concentration giving rise to these capturing events can be determined by using the appropriate statistical models based on a Poisson process. Moreover, the smaller the cell size, the larger the number of cells on the surface 190, the more accurate extraction of the target concentration using the Poisson statistical model becomes.

In embodiments of the present disclosure the surface 190 (i.e. the sensing area) comprises about 20000 capture sites per $\mu m^2$. When a detector with a cell size of 1 $\mu m^2$ is provided, and when the target concentration and the incubation time are large such that a large fraction of the capture sites are occupied, this would result in a "continuous" signal (up to 20000 bindings possible), and the approach described above would not work. However, under these conditions the signal itself is large, and the signal-to-noise ratio may already be large enough to get an accurate concentration value without recourse to the technique described above. On the other hand, when the target concentration and/or the incubation time are smaller, the signal decreases and the signal-to-noise ratio becomes worse. However, it is precisely in this regime that the described technique becomes applicable. In order to obtain a digital result in the concentration range of interest (e.g. determined by the known concentration range of the target in healthy or ill patients, or the concentration range of the target in a bioreactor), the cell size of the detector can be chosen according to embodiments of the present disclosure.

In an exemplary embodiment of the present disclosure the sensor device 100 is an immunological sensor (antibody-based protein sensor). The typical density of capture sites on the surface 190 is $\Gamma_{capture\ probes}$=10 000 to 20 000 $\mu m^{-2}$. In the following numerical example $10^4\ \mu m^{-2}$ is taken.

A typical association rate constant is:

$k_{on}=10^5 M^{-1} s^{-1}$.

A typical concentration for a low-abundant target molecule is:

[target]=1 pM=$10^{-12}$ M.

The association rate in this case is:

$$r_{association} = k_{on} \times \Gamma_{capture\ probes} \times [target]$$
$$= 10^5 M^{-1} s^{-1} \times 10^4 \mu m^{-2} \times 10^{-12} M$$
$$= 10^{-3} \mu m^{-2} s^{-1}$$

In other words, 0.001 binding events per second on a 1×1 $\mu m^2$ capture area, or 0.1 binding events per second on a 10×10 $\mu m^2$ capture area.

The order of magnitude of the detection antibody concentration in a sandwich ELISA assay is ~10 nM=$10^{-8}$ M. Assuming a transducer which is sensitive to the first 100 nm above its surface, then the number of background molecules in the detection volume above a 1 $\mu m^2$ detector area is:

$$10^{-8} M \times (1\ \mu m)^2 \times 100\ nm =$$
$$10^{-8} \times 6.02\ 10^{23} dm^{-3} \times (10^{-4} dm)^2 \times 100\ 10^{-7} dm = 600\ \mu m^{-2}$$

The characteristic time scale for these background events is the time to diffuse over 100 nm=100 $10^{-7}$ cm (i.e. in or out of the detection volume). A typical diffusion coefficient for proteins in water is D=$10^{-5}$ cm$^2$ s$^{-1}$. With a diffusion length given by $L_D$=sqrt(D t), the time required to diffuse over length $L_D$ is t=$L_D^2$/D=(100 $10^{-7}$ cm)$^2$/($10^{-5}$ cm$^2$ s$^{-1}$)=$10^{-5}$ s.

In other words, for integration times much longer than 10 us, the background intensity of 600 $\mu m^{-2}$ would be significantly averaged out. In this particular case, discrete events can be distinguished for detection areas roughly around 1 $\mu m^2$ ($10^{-3}$ events per second per detector), or in the approximate range of (0.1 $\mu m$)$^2$ ($10^{-5}$ events per second per detector) to (10 $\mu m$)$^2$ (0.1 events per second per detector).

In embodiments of the present disclosure luminescent targets with large labels are used to increase the signal per binding event. These labels may be beads with a large number of fluorophores.

The signal per binding event may also be increased by increasing the number of fluorophores which can be bound with the secondary antibody. This may for example be larger than 10, or even larger than 20, or even around 100. In example embodiments of the present disclosure, the luminescence of a target can be increased by increasing the number of luminescent molecules which can bind with the target.

Figure 10:
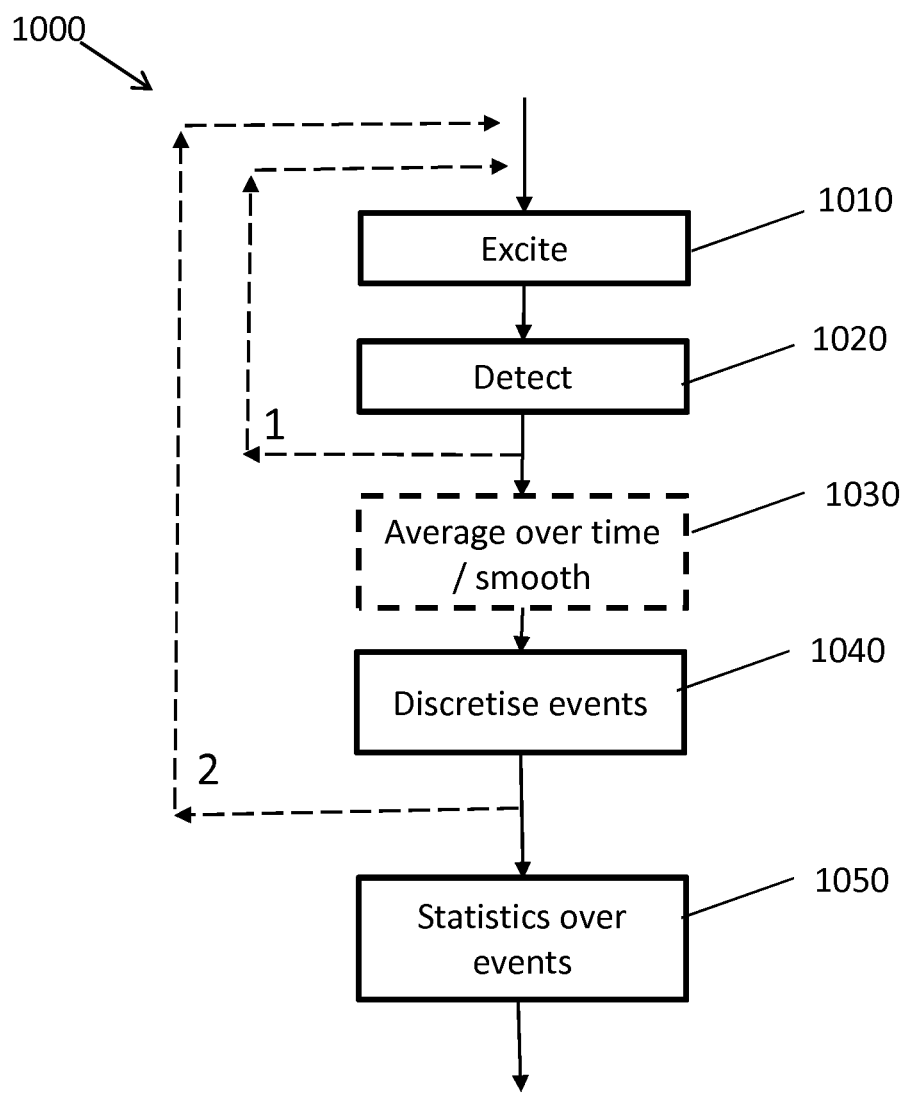
FIG. 10 shows different steps in a method for quantifying luminescent targets in accordance with embodiments of the present disclosure.

In a second aspect, the present disclosure provides a method for quantifying luminescent targets, for instance for detecting presence, for determining an absolute value or for determining concentration. FIG. 10 shows the different steps of a method 1000 according to embodiments of the present disclosure.

In a first step 1010 the luminescent targets are excited. Thereby the luminescent targets generate a luminescence signal.

In a second step 1020 the luminescence signal generated by the luminescent targets is measured per cell, wherein the monitored volume may be subdivided in a number of cells. The measured luminescence signal for each cell comprises a desired signal emanating from the luminescent targets in that cell and a background signal. The detection is done on a space and/or time resolution which is so high that the total amount of luminescent targets/or the increase of luminescent targets compared to the previous detection is limited (e.g. less than 20, or even less than 10, or even less than 3, or even zero or 1).

In embodiments of the present disclosure the excitation 1010 and detection 1020 steps may be repeated in an optional loop (loop 1 in FIG. 10) such that there are enough datapoints for the next optional smoothing/averaging step 1030.

The excitation 1010 and detection 1020 steps may be followed by an optional smoothing/averaging 1030 to reduce the uncertainty on the measurement. In the example illustrated in FIG. 6 to FIG. 9 this results in the thick error bars 620.

Smoothing and averaging 1030 can be done at one timepoint along the accumulation curve (e.g. if endpoint measurements are done; i.e. when the accumulation has stopped) on an array of small cells. Then the smoothing and averaging is done for each cell. Smoothing and averaging 1030 may also be done at different timepoints along the accumulation curve. Then the averaging and smoothing can be done on successive sets of e.g. 10 or 100 repetitions of loop 1, or also using a sliding window of e.g. 10 or 100 repetitions of loop 1.

After the detection step 1020 or optionally after the smoothing and averaging step 1030, the following step is to discretize 1040 the events (in each spatial cell and/or along the time axis).

After discretization 1040 the sequence may be started again with an excitation step 1010 thus forming a closed loop 2. This is an optional loop. Discretization 1040 may also be an offline process. In that case loop 2 may coincide with loop 1 (first gathering the data, and next applying an offline discretization step on this data. Loops 1 and 2 may not be required in case only spatial statistics are to be provided, and if averaging is not required to reduce the noise (see for example the simulation results illustrated in FIG. 6 to FIG. 9).

The discretization step 1040 is followed by applying statistical methods (e.g. Poisson statistics) 1050 on the many cells and/or time points to deduce/determine the concentration of the target. This step may include finding out which measured signal level corresponds to zero specifically bound molecules.

Devices 100 according to embodiments of the present disclosure may be used in bioreactors. Bioreactors are, for example, used in the pharmaceutical industry, in food and agriculture (e.g. beer), in cell and tissue culturing (e.g. stem cells, regenerative medicine). In those cases, (affinity-based) (bio)sensor devices 100, according to the present disclosure, can be used to monitor if the culture is performing fine (e.g. check nutrients, measure the concentration of a product the culture is fabricating, check for contaminations).

The invention claimed is:

1. A sensor device for quantifying luminescent targets, wherein the device comprises:
a light source for exciting the luminescent targets, thus generating luminescence signals;
a detector adapted for detecting the luminescence signals of the luminescent targets in a cell, resulting in a detected signal which comprises a desired signal originating from the luminescent targets in the cell and a background signal,
wherein the detector has a spatial cell resolution and/or has a time resolution that is above a predefined threshold such that 20 or less of the luminescent targets will be present in the cell when measuring at low target concentration and/or that the time between two measurements is below a predetermined threshold level such that 20 or less of the luminescent targets add to the cell in between two measurements, and
wherein a change in the number of the luminescent targets in the cell results in an observable change in the detected signal; and
a processor configured to distinguish the desired signal from the background signal and to combine the detected signals of the different cells and/or different moments in time, so as to quantify the luminescent targets.

2. The sensor device according to claim 1, wherein a size of the cell is below a predefined threshold such that a total background level decreases, and discrete events become distinguishable after processing by the processor.

3. The sensor device according to claim 1, wherein luminescent targets added to the observed cell in between two sample moments increase the desired signal within a discrete step.

4. The sensor device according to claim 1, wherein the spatial cell resolution is above a predefined threshold such that only a less than a minimum number of the luminescent targets will be present in the cell when measuring at low target concentration and that an uncertainty on the desired signal when a luminescent target is present is smaller than the change in desired signal for a change in number of targets by one target.

5. The sensor device according to claim 4, wherein the processor is configured to compare the measured signal of an observed cell with at least one adjustable threshold such that an exact number of luminescent targets present in the observed cell can be concluded.

6. The sensor device according to claim 1, the sensor device further comprising a surface or a three dimensional volume, wherein the surface or the three dimensional volume comprises affinity probes for capturing the luminescent targets.

7. The sensor device according to claim 6, the sensor device further comprising: an evanescent field generating structure, wherein the light source is coupled to the evanescent field generating structure, and wherein the evanescent field generating structure is adapted for generating an evanescent field at the surface or in the three dimensional volume.

8. The sensor device according to claim 1, adapted for use with fluorescent targets.

9. A method for quantifying luminescent targets, the method comprising: exciting the luminescent targets to generate a luminescence signal; detecting per cell a measured luminescence signal, wherein the measured luminescence signal comprises a desired signal emanating from the luminescent targets in the cell and a background signal, and wherein the detecting is done on a cell space and/or time resolution which is above a predefined threshold level such that a total number of the luminescent targets is 20 or less or an increase of the luminescent targets with regard to that of a previous detection is 20 or less; and a discretizing step thereby obtaining the total number of the luminescent targets or the increase of the luminescent targets per cell.

10. The method according to claim 9, wherein statistical methods are applied to the obtained target numbers over a plurality of cells and/or wherein the exciting, detecting, and discretizing steps are executed at a plurality of time points, and wherein statistical methods are applied to the obtained target numbers at the plurality of time points so as to quantify the luminescent targets in the original sample.

11. The method according to claim 9, the method further comprising an averaging step and/or smoothing step after the detection step, wherein the averaging step and/or smoothing step is applied on data obtained by the at least one executed exciting step and detecting step.

* * * * *